United States Patent
Saint et al.

(10) Patent No.: US 9,867,937 B2
(45) Date of Patent: Jan. 16, 2018

(54) SYSTEM AND METHOD FOR MITIGATING RISK IN AUTOMATED MEDICAMENT DOSING

(71) Applicant: Tandem Diabetes Care, Inc., San Diego, CA (US)

(72) Inventors: Sean Saint, San Diego, CA (US); Michael Rosinko, Anaheim, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 610 days.

(21) Appl. No.: 14/479,994

(22) Filed: Sep. 8, 2014

(65) Prior Publication Data

US 2015/0073337 A1 Mar. 12, 2015

Related U.S. Application Data

(60) Provisional application No. 61/874,428, filed on Sep. 6, 2013.

(51) Int. Cl.
*A61M 5/172* (2006.01)
*G06F 19/00* (2011.01)
*A61M 5/142* (2006.01)

(52) U.S. Cl.
CPC ...... *A61M 5/1723* (2013.01); *A61M 5/14244* (2013.01); *G06F 19/345* (2013.01); *G06F 19/3468* (2013.01); *A61M 2005/14208* (2013.01); *A61M 2205/3523* (2013.01); *A61M 2205/502* (2013.01); *A61M 2205/52* (2013.01);

(Continued)

(58) Field of Classification Search
CPC ....... A61M 25/02; A61M 5/142; A61B 5/684; A61B 5/418; A61B 5/415; A61B 5/14865
See application file for complete search history.

(56) References Cited

U.S. PATENT DOCUMENTS

| | | | |
|---|---|---|---|
| 5,558,638 A | 9/1996 | Evers et al. | |
| 5,919,216 A * | 7/1999 | Houben | A61B 5/14532 607/72 |
| 5,997,475 A | 12/1999 | Bortz | |

(Continued)

FOREIGN PATENT DOCUMENTS

WO     WO 2009/023406 A1     2/2009

OTHER PUBLICATIONS

PCT Search Report and Written Opinion dated Dec. 16, 2014 for PCT Application No. PCT/US2014/054559 filed Sep. 8, 2014, 17 pages.

(Continued)

*Primary Examiner* — Imani Hayman
*Assistant Examiner* — Matthew A Engel
(74) *Attorney, Agent, or Firm* — Patterson Thuente Pedersen, P.A.

(57) ABSTRACT

A portable infusion pump can communicate with glucose monitor, such as a continuous glucose monitor (CGM), to receive continuous feedback relating to a user's blood glucose level during insulin or other medicament therapy and can automatically deliver insulin to a user when the CGM data indicates a need for additional insulin. Due to potential unreliability in the correlation of the CGM data to the user's actual blood glucose level, risk mitigation can be employed to limit the amount of extra insulin that can be delivered by the pump in response to the CGM data.

14 Claims, 7 Drawing Sheets

(52) U.S. Cl.
CPC ... *A61M 2209/01* (2013.01); *A61M 2230/005* (2013.01); *A61M 2230/201* (2013.01)

(56) References Cited

U.S. PATENT DOCUMENTS

| | | | |
|---|---|---|---|
| 6,505,059 B1 | 1/2003 | Kollias et al. | |
| 6,852,104 B2 * | 2/2005 | Blomquist | A61M 5/1452 604/504 |
| 6,862,466 B2 | 3/2005 | Ackerman | |
| 7,022,072 B2 | 4/2006 | Fox et al. | |
| 7,378,270 B2 | 5/2008 | Azarnia et al. | |
| 7,399,277 B2 | 7/2008 | Saidara et al. | |
| 7,460,895 B2 | 12/2008 | Arnold et al. | |
| 7,497,827 B2 | 3/2009 | Brister et al. | |
| 7,524,287 B2 | 4/2009 | Bharmi | |
| 7,591,801 B2 | 9/2009 | Brauker et al. | |
| 7,711,402 B2 | 5/2010 | Shults et al. | |
| 7,713,574 B2 | 5/2010 | Brister et al. | |
| 7,734,323 B2 | 6/2010 | Blomquist et al. | |
| 7,751,907 B2 | 7/2010 | Blomquist | |
| 7,764,170 B2 | 7/2010 | Yi | |
| 7,766,830 B2 | 8/2010 | Fox et al. | |
| 7,774,145 B2 | 8/2010 | Brauker et al. | |
| 7,778,680 B2 | 8/2010 | Goode, Jr. et al. | |
| 7,779,183 B2 | 8/2010 | Koehler et al. | |
| 7,797,028 B2 | 9/2010 | Goode, Jr. et al. | |
| 7,806,854 B2 | 10/2010 | Damiano et al. | |
| 7,914,450 B2 | 3/2011 | Goode, Jr. et al. | |
| 7,925,321 B2 | 4/2011 | Goode et al. | |
| 7,933,639 B2 | 4/2011 | Goode et al. | |
| 7,955,261 B2 | 6/2011 | Goode et al. | |
| 7,959,569 B2 | 6/2011 | Goode et al. | |
| 7,976,492 B2 | 7/2011 | Brauker et al. | |
| 7,979,104 B2 | 7/2011 | Kamath et al. | |
| 7,986,986 B2 | 7/2011 | Goode et al. | |
| 8,052,601 B2 | 11/2011 | Goode, Jr. et al. | |
| 8,090,435 B2 | 1/2012 | Gill et al. | |
| 8,114,350 B1 | 2/2012 | Silver et al. | |
| 8,208,984 B2 | 6/2012 | Blomquist et al. | |
| 8,219,222 B2 | 6/2012 | Blomquist | |
| 8,221,345 B2 | 7/2012 | Blomquist | |
| 8,251,906 B2 | 8/2012 | Brauker et al. | |
| 8,287,495 B2 | 10/2012 | Michaud et al. | |
| 8,290,562 B2 | 10/2012 | Goode, Jr. et al. | |
| 8,311,749 B2 | 11/2012 | Brauker et al. | |
| 8,332,008 B2 | 12/2012 | Goode et al. | |
| 8,346,399 B2 | 1/2013 | Blomquist et al. | |
| 8,369,919 B2 | 2/2013 | Kamath et al. | |
| 8,460,231 B2 | 6/2013 | Brauker et al. | |
| 8,562,558 B2 | 7/2013 | Yodfat et al. | |
| 8,573,027 B2 | 11/2013 | Rosinko et al. | |
| 8,657,779 B2 | 2/2014 | Blomquist | |
| 8,753,316 B2 | 6/2014 | Blomquist | |
| 8,882,701 B2 | 11/2014 | DeBelser et al. | |
| 8,986,253 B2 | 3/2015 | DiPerna | |
| 2002/0193679 A1 * | 12/2002 | Malave | A61M 5/172 600/407 |
| 2003/0225360 A1 * | 12/2003 | Eppstein | A61M 37/0015 604/19 |
| 2004/0054263 A1 | 3/2004 | Moerman et al. | |
| 2005/0027182 A1 | 2/2005 | Siddiqui et al. | |
| 2006/0229502 A1 * | 10/2006 | Pollock | A61B 5/14532 600/300 |
| 2007/0066956 A1 * | 3/2007 | Finkel | A61M 5/142 604/500 |
| 2008/0114228 A1 | 5/2008 | Mccluskey et al. | |
| 2008/0171967 A1 | 7/2008 | Blomquist et al. | |
| 2008/0172029 A1 | 7/2008 | Blomquist | |
| 2008/0172031 A1 | 7/2008 | Blomquist | |
| 2008/0228056 A1 | 9/2008 | Blomquist et al. | |
| 2008/0306434 A1 | 12/2008 | Dobbles et al. | |
| 2008/0306444 A1 | 12/2008 | Brister et al. | |
| 2009/0105636 A1 | 4/2009 | Hayter et al. | |
| 2009/0192366 A1 | 7/2009 | Mensinger et al. | |
| 2009/0192724 A1 | 7/2009 | Brauker et al. | |
| 2009/0192745 A1 | 7/2009 | Kamath et al. | |
| 2009/0240193 A1 | 9/2009 | Mensinger et al. | |
| 2010/0056993 A1 | 3/2010 | Chase | |
| 2010/0057040 A1 * | 3/2010 | Hayter | A61M 5/14244 604/504 |
| 2010/0121169 A1 | 5/2010 | Petisce et al. | |
| 2010/0168543 A1 | 7/2010 | Kamath et al. | |
| 2010/0179402 A1 | 7/2010 | Goode, Jr. et al. | |
| 2010/0218586 A1 | 9/2010 | Rosinko et al. | |
| 2010/0262434 A1 | 10/2010 | Shaya | |
| 2010/0298765 A1 | 11/2010 | Budiman et al. | |
| 2011/0029269 A1 | 2/2011 | Hayter et al. | |
| 2011/0071464 A1 * | 3/2011 | Palerm | A61B 5/14532 604/66 |
| 2011/0106049 A1 | 5/2011 | Damiano et al. | |
| 2011/0190614 A1 | 8/2011 | Brister et al. | |
| 2011/0224523 A1 * | 9/2011 | Budiman | A61B 5/14532 600/365 |
| 2011/0257895 A1 | 10/2011 | Brauker et al. | |
| 2012/0059353 A1 | 3/2012 | Kovatchev et al. | |
| 2012/0232484 A1 | 9/2012 | Blomquist | |
| 2012/0232521 A1 | 9/2012 | Blomquist | |
| 2012/0265722 A1 | 10/2012 | Blomquist | |
| 2013/0053816 A1 | 2/2013 | DiPerna et al. | |
| 2013/0158504 A1 | 6/2013 | Ruchti et al. | |
| 2013/0324928 A1 | 12/2013 | Kruse | |
| 2013/0331790 A1 | 12/2013 | Brown et al. | |
| 2014/0171772 A1 | 6/2014 | Blomquist | |
| 2014/0273042 A1 | 9/2014 | Saint | |
| 2014/0276419 A1 | 9/2014 | Rosinko et al. | |
| 2014/0276420 A1 | 9/2014 | Saint | |
| 2014/0276556 A1 | 9/2014 | Saint et al. | |
| 2014/0276574 A1 | 9/2014 | Saint | |
| 2014/0350371 A1 | 11/2014 | Blomquist et al. | |
| 2014/0378898 A1 | 12/2014 | Rosinko | |
| 2016/0030669 A1 | 2/2016 | Harris et al. | |
| 2016/0082188 A1 | 3/2016 | Blomquist et al. | |
| 2016/0199571 A1 | 7/2016 | Rosinko et al. | |

OTHER PUBLICATIONS

Search Report dated Mar. 28, 2017 for EP Application No. 14842267.8, 7 pages.

* cited by examiner

SYSTEM AND METHOD FOR MITIGATING RISK IN AUTOMATED MEDICAMENT DOSING

RELATED APPLICATION

The present application claims the benefit of U.S. Provisional Application No. 61/874,428 filed Sep. 6, 2013, which is incorporated herein by reference in its entirety.

FIELD OF THE INVENTION

The present invention relates to ambulatory infusions pumps and, more particularly, to mitigating risk when integrating features of continuous glucose monitoring with infusion pumps.

BACKGROUND

There are many applications in academic, industrial, and medical fields that benefit from devices and methods that are capable of accurately and controllably delivering fluids, such as liquids and gases that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both type I and type II diabetes. Some pumps configured as portable infusion devices can provide continuous subcutaneous medicament injection and/or infusion therapy for the treatment of diabetes. Such therapy may include, e.g., the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. patent application Ser. No. 13/838,617, U.S. patent application Ser. No. 13/827,707 and U.S. Pat. No. 8,287,495, each of which is incorporated herein by reference in its entirety.

Portable infusion pumps for delivering insulin or other medicaments can be used in conjunction with continuous glucose monitoring (CGM) devices. A CGM provides a substantially continuous estimated blood glucose level through a transcutaneous sensor that measures analytes, such as glucose, in the patient's interstitial fluid rather than the patient's blood. CGM systems typically consist of a transcutaneously-placed sensor, a transmitter and a monitor. A CGM system allows a patient or caregiver to insert a single sensor probe under the skin for multiple days. Thus, the patient is only required to perform a single moderately invasive action with a single entry point in the subdermal layer on, e.g., a weekly basis.

Ambulatory infusion pumps typically allow the patient or caregiver to adjust the amount of insulin or other medicament delivered, by a basal rate or a bolus, based on blood glucose data obtained by a blood glucose meter or CGM. Some ambulatory infusion pumps may include the capability to interface with a BGM or CGM such as, e.g., by receiving measured or estimated blood glucose levels and prompting the user to adjust the level of medicament being administered or planned for administration or, in cases of abnormally low blood glucose readings, prompting temporary cessation of insulin administration. These portable pumps may incorporate a BGM or CGM within the hardware of the pump or may communicate with a dedicated BGM or CGM via wired or wireless data communication protocols. Such pumps may be particularly important in facilitating patient compliance and improved or more accurate treatment of diabetes. One example of integration of infusion pumps with CGM devices is described in U.S. patent application Ser. No. 13/800,453, which is hereby incorporated by reference herein.

The delivery of insulin or other medicament from a portable infusion pump making use of CGM data necessitates accurate and reliable CGM data output. CGM devices are therefore calibrated with blood samples to correlate actual blood glucose data with the CGM readings. However, such calibrations are only done periodically, such as every 12 hours, and the longer it has been since a calibration the more likely the CGM is unreliable to some degree and the more unreliable the CGM is likely to become until the next calibration.

Insulin or other medicament dosing by basal rate and/or bolus techniques could automatically be provided by a pump based on readings received into the pump from a CGM device that is, e.g., external to the portable insulin pump or integrated with the pump as a pump-CGM system in a closed-loop fashion. With respect to insulin delivery, some systems including this feature are can be referred to as artificial pancreas systems because the systems serve to mimic biological functions of the pancreas for patients with diabetes. However, there are a number of risks in automatically dosing insulin, or other medicaments, based on CGM readings that can become inaccurate or unreliable. For example, a CGM reading or readings may indicate that a user's blood glucose level is high and therefore the pump may automatically deliver a bolus of medicament or increase the basal rate to lower the user's blood glucose to a target level. However, if the CGM reading is inaccurately high, the extra insulin may actually lower the user's blood glucose level below a desired target level, possibly to a dangerously low level. This problem may not be detected until the CGM is next calibrated, perhaps not for several hours. Thus, automatically dosing medicaments such as insulin based on CGM readings can have potentially dangerous effects in situations where the CGM readings are inaccurate or unreliable relative to the user's actual blood glucose levels.

SUMMARY OF THE INVENTION

A portable infusion pump can communicate with glucose monitor, such as a a continuous glucose monitor (CGM), to receive continuous feedback relating to a user's blood glucose level during insulin or other medicament therapy and can automatically deliver insulin to a user when the CGM data indicates a need for additional insulin. Due to potential unreliability in the correlation of the CGM data to the user's actual blood glucose level, risk mitigation can be employed to limit the amount of extra insulin that can be delivered by the pump in response to the CGM data.

In some embodiments, risk of potentially unreliable CGM readings in automatic insulin or other medicament dosing based on the readings is mitigated by limiting an amount of excess insulin that can be delivered over a previous bolus or basal rate for a predefined period of time after the previous bolus was delivered or basal rate delivery sequence or protocol was initiated. In one embodiment, a basal rate increase based on CGM data can be limited to a defined percentage increase over the previous basal rate. In other embodiments, excess insulin following delivery of a bolus can be limited based on either a fixed amount of additional units of insulin or a fixed percentage of the previous bolus. Such limits can be set globally for all basal rates and/or boluses or can be set individually upon delivery of a bolus or basal rate.

In other embodiments, automatic insulin or other medicament dosing risk can be mitigated based on a time constraint that limits the amount of time that automated insulin dosing is allowed to be active. When an auto-dosing threshold or limit is reached, automatic dosing can be automatically disabled. In one embodiment, auto-dosing can be disabled a set amount of time after the most recent calibration of the CGM. In another embodiment, auto-dosing can be disabled when the predicted maximum error of the CGM, based on, e.g., CGM manufacturer data or other relevant information, reaches a predetermined threshold. In a further embodiment, reaching a maximum deviation between the patient's blood glucose level at the most recent calibration point and the current blood glucose level as indicated by the CGM data can automatically disable auto-dosing.

In further embodiments, risk mitigation for automatic insulin or other medicament dosing based on CGM data can vary based on the predicted maximum error for the CGM at a given time. An algorithm can be employed that initially calculates a desired drop in blood glucose based on the CGM data. Because the user's actual blood glucose could be lower than that indicated by the CGM data by as much as the maximum CGM error at the given time, the maximum error is subtracted from the desired drop. The insulin dose for delivery to the user is then calculated based on this adjusted value for the attempted blood glucose drop in order to avoid the possibility of dropping the user's blood glucose too low. A similar concept could be applied in this and other embodiments of the invention in which risks associated with the delivery of a medicament that raises glucose level, such as glucagon, can be mitigated when a predicted maximum error of the CGM, for example, indicates that delivery could cause the glucose level could become dangerously high.

Certain embodiments are described further in the following description, examples, claims, and drawings. These embodiments will become more apparent from the following detailed description when taken in conjunction with the accompanying exemplary drawings.

DETAILED DESCRIPTION

Provided herein are systems, devices and methods for mitigating risk in automatically dosing insulin to patients based on readings from continuous glucose monitoring devices. Some embodiments may include advances in the internal components, the control circuitry, and improvements in a user interface of the systems and devices. The advances may allow for a safer and more accurate delivery of medicament to a patient than is attainable from other devices, systems, and methods.

Figure 1:
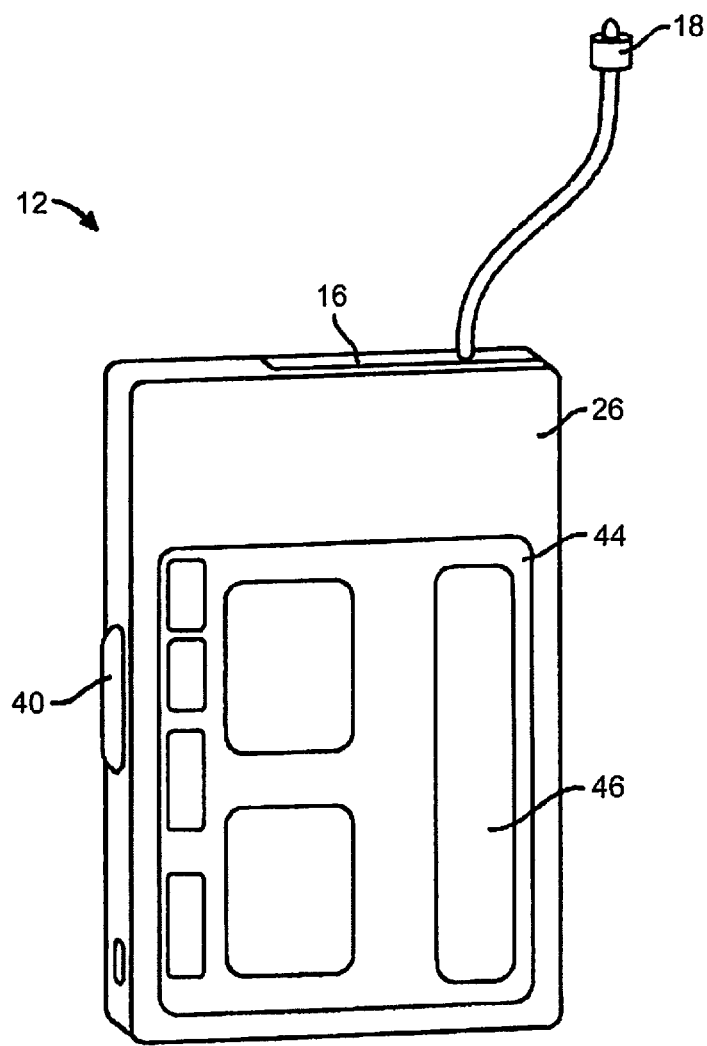
FIG. 1 is a perspective view of an infusion pump according to an embodiment of the present invention.

FIG. 1 depicts an embodiment of a medical device that can be used with embodiments of the present invention. In this embodiment, the medical device is configured as a pump 12, such as an infusion pump, that can include an internal pumping or delivery mechanism and reservoir for delivering medicament such as insulin to a patient and an output/display 44. The type of output/display 44 may vary as may be useful for a particular application. The type of visual output/display may include LCD displays, LED displays, plasma displays, graphene-based displays, OLED displays and the like. The output/display 44 may include an interactive and/or touch sensitive screen 46 having an input device such as, for example, a touch screen comprising a capacitive screen or a resistive screen. The pump 12 may additionally include a keyboard or other input device known in the art for data entry, which may be separate from the display. The pump 12 may additionally include one or more of a keyboard, microphone, or other input device known in the art for data entry, which such input device or devices may be separate from the display. The pump 12 may also include a capability to operatively couple to a secondary display device such as a remote display, a remote control device, a laptop computer, personal computer, tablet computer, mobile communication device such as a smartphone or personal digital assistant (PDA) or the like.

In one embodiment, the medical device can be a portable insulin pump configured to deliver insulin to a patient. Further details regarding such pump devices can be found in U.S. Patent Application No. 2011/0144586, which is incorporated herein by reference. In other embodiments, the medical device can be an infusion pump configured to deliver one or more additional or other medicaments to a patient. In a further embodiment, the medical device can include a glucose meter such as continuous glucose monitor. In other embodiments, the medical device can additionally or separately monitor one or more other physiological parameters of a patient.

Figure 2:
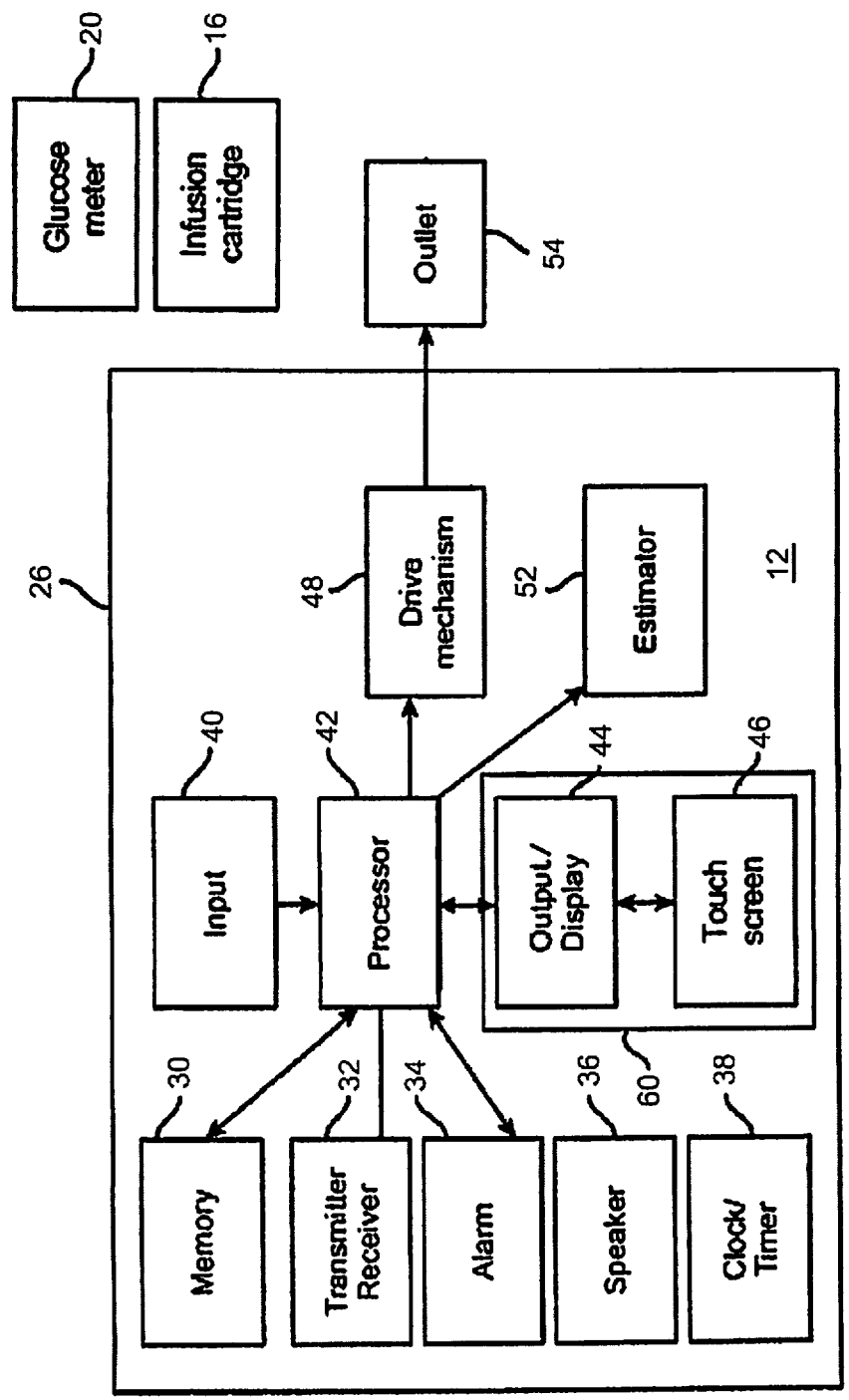
FIG. 2 is a block diagram representing an embodiment of an infusion pump according to the present invention.

FIG. 2 illustrates a block diagram of some of the features that can be used with embodiments of the present invention, including features that may be incorporated within the housing 26 of a medical such as the pump 12. The pump 12 includes a processor 42 that functions to control the overall functions of the device. The infusion pump 12 may also include, e.g., a memory device 30, a communications device such as a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. The memory device 30 may be coupled to the processor 42 to receive and store input data and to communicate that data to the processor 42. The input data may include user input data and non-user/sensor input data. The input data from the memory device 30 may be used to generate therapeutic parameters for the infusion pump 12. The GUI 60 may be configured for displaying a request for the user to input data and for receiving user input data in response to the request, and communicating that data to the memory.

The processor 42 may communicate with and/or otherwise control the drive mechanism, output/display, memory, a transmitter/receiver and other components. In some embodiments, the processor 42 may communicate with another processor within the pump 12 and/or one or more processors of other devices, for example, a continuous glucose monitor (CGM), display device, smartphone, etc. through the transmitter/receiver. The processor 42 may include programming that can be run to control the infusion of insulin or other medicament from the cartridge, the data to be displayed by the display, the data to be transmitted via the transmitter, etc. The processor 42 may also include programming that may allow the processor to receive signals and/or other data from an input device, such as a sensor that may sense pressure, temperature or other parameters.

The processor 42 may also include additional programming to allow the processor 42 to learn user preferences and/or user characteristics and/or user history data. This information can be utilized to implement changes in use, suggestions based on detected trends, such as, weight gain or loss. The processor can also include programming that allows the device to generate reports, such as reports based upon user history, compliance, trending, and/or other such data. Additionally, infusion pump device embodiments of the disclosure may include a "power off" or "suspend" function for suspending one or more functions of the device, such as, suspending a delivery protocol, and/or for powering off the device or the delivery mechanism thereof. For some embodiments, two or more processors may be used for controller functions of the infusion pumps, including a high power controller and a low power controller used to maintain programming and pumping functions in low power mode, in order to save battery life.

The memory device 30 may be any type of memory capable of storing data and communicating that data to one or more other components of the device, such as the processor. The memory may be one or more of a Flash memory, SRAM, ROM, DRAM, RAM, EPROM and dynamic storage, for example. For instance, the memory may be coupled to the processor and configured to receive and store input data and/or store one or more templates or generated delivery patterns. For example, the memory can be configured to store one or more personalized (e.g., user defined) delivery profiles, such as a profile based on a user's selection and/or grouping of various input factors, past generated delivery profiles, recommended delivery profiles, one or more traditional delivery profiles, e.g., square wave, dual square wave, basal and bolus rate profiles, and/or the like. The memory can also store, for example, user information, history of use, glucose measurements, compliance and an accessible calendar of events. The memory can also store limits on insulin doses that can be delivered based on CGM data, as discussed herein. The housing 26 of the pump 12 may be functionally associated with an interchangeable and removable glucose meter 20 and/or one or more infusion cartridges 16. The infusion cartridge 16 may have an outlet port 54 that may be connected to an infusion set (not shown) via an infusion set connector 18. Further details regarding some embodiments of various infusion pumps can be found in U.S. Patent Application No. 2011/0144586, which is hereby incorporated by reference in its entirety.

Figure 3:
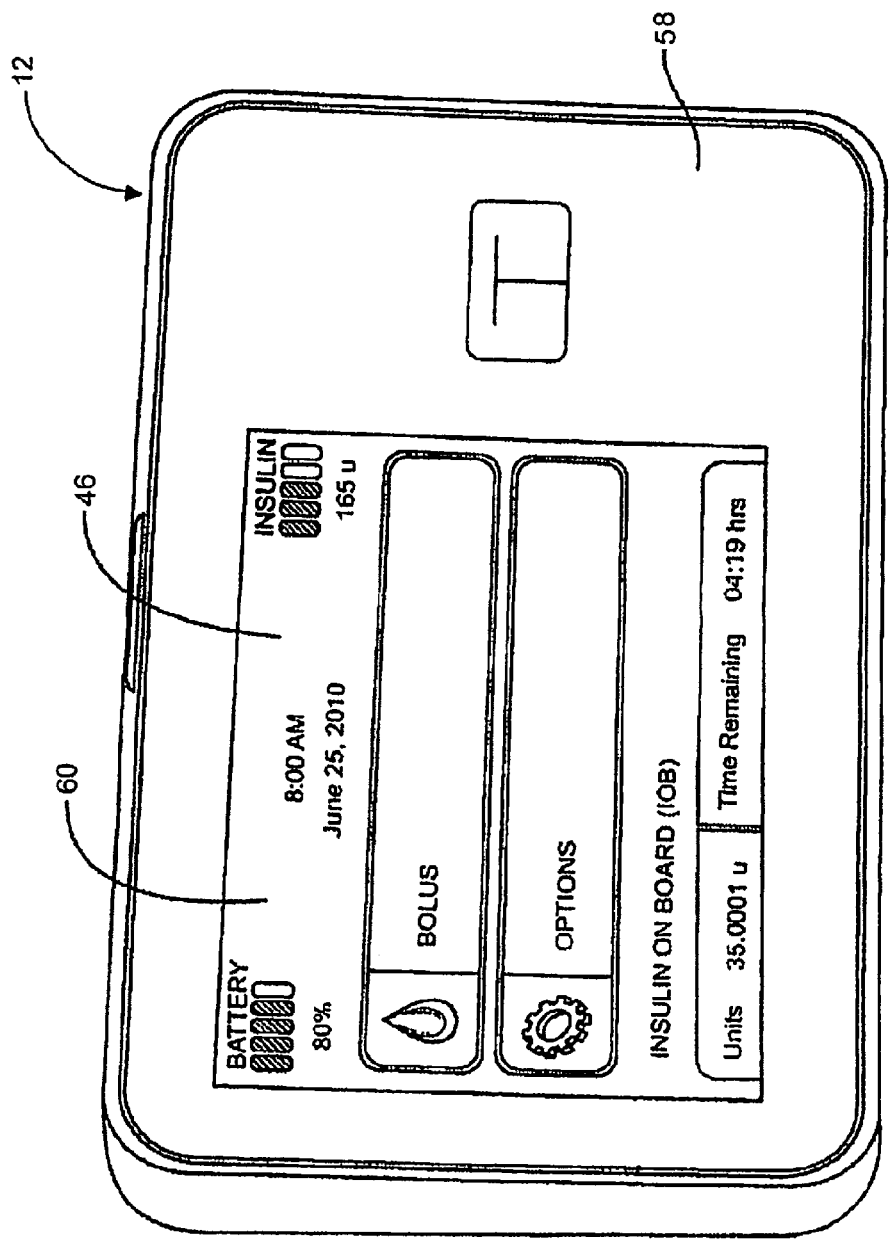
FIG. 3 depicts a screen shot of a home screen page of a graphical user interface of an infusion pump according to an embodiment of the present invention.

Referring to FIG. 3, a front view of pump 12 is depicted. The pump 12 may include a user interface, such as, for example, a user-friendly GUI 60 on a front surface 58 or other location of pump 12. The GUI 60 may include a touch-sensitive screen 46 that may be configured for displaying data, facilitating data and/or command entry, providing visual tutorials, as well as other interface features that may be useful to the patient operating the pump 12. The GUI can also present alarm or alerts to the user.

Figure 4:
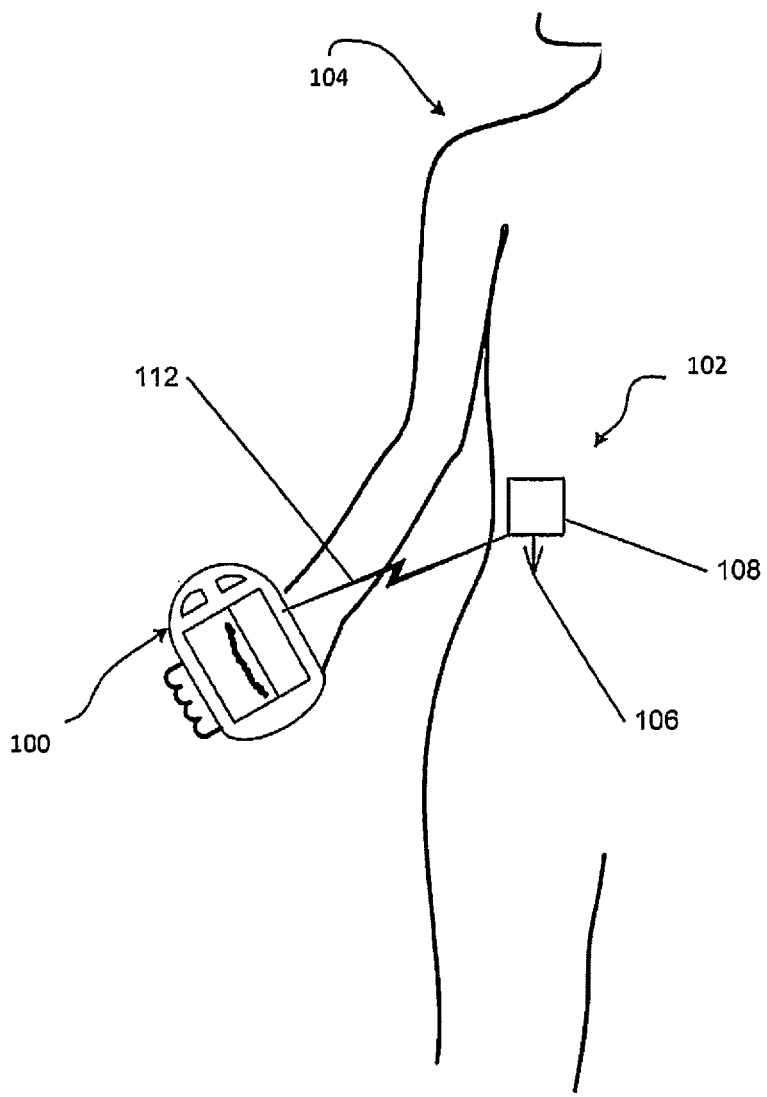
FIG. 4 is a partial schematic view depicting a continuous glucose monitor according to an embodiment of the present invention deployed on a patient.

Pump 12 can interface with a glucose meter, such as a continuous glucose monitor (CGM), that provides a substantially continuous estimated glucose level through a transcutaneous sensor that measures analytes, such as glucose, in the patient's interstitial fluid rather than the patient's blood. Referring to FIG. 4, an exemplary CGM system 100 according to an embodiment of the present invention is shown (other CGM systems can be used). The illustrated CGM system 100 includes a sensor 102 affixed to a patient 104 and is associated with the insulin infusion device 12. The sensor 102 includes a sensor probe 106 configured to be inserted to a point below the dermal layer (skin) of the patient 104. The sensor probe 106 is therefore exposed to the patient's interstitial fluid or plasma beneath the skin and reacts with that interstitial fluid to produce a signal that can be calibrated with the patient's blood glucose (BG) level. The sensor 102 includes a sensor body 108 that transmits data associated with the interstitial fluid to which the sensor probe is exposed. The data may be transmitted from the sensor 102 to the glucose monitoring system 100 via a wireless transmitter, such as a near field communication (NFC) radio frequency (RF) transmitter or a transmitter operating according to a "WiFi" or "Bluetooth" protocol or the like, or the data may be transmitted via a wire connector from the sensor 102 to the monitor system 100. Transmission of sensor data to the glucose monitor system 100 by wireless or wired connection is represented in FIG. 4 by the arrow line 112. Further detail regarding such systems and definitions of related terms can be found in, e.g., U.S. Pat. Nos. 8,311,749, 7,711,402 and 7,497,827, each of which is hereby incorporated by reference in its entirety.

In one embodiment, part of the CGM system 100 is incorporated into the pump 12 such that the processor 42 is adapted to receive the data from the sensor 102 and process and display the data on the display 44. In another embodiment, the CGM 100 is a separate device that communicates with the pump 12 through a wired or wireless link to transmit the CGM data to the pump 12.

In an embodiment of a pump 12 that communicates with a CGM and that integrates CGM data and pump data as described herein, the CGM can automatically transmit the glucose data to the pump. The pump can then automatically determine therapy parameters based on the data. For example, if the CGM data indicates that the user's blood glucose level is over a high blood glucose threshold level stored in memory, the pump can automatically calculate an insulin or other medicament bolus amount or an increase to a basal rate to bring the user's blood glucose level below the threshold or to a target value. As with other parameters related to therapy, such thresholds and target values can be stored in memory located in the pump or, if not located in the pump, stored in a separate location and accessible by the pump processor (e.g., "cloud" stored values accessible via a network connection). The pump processor can periodically and/or continually execute instructions for a checking function that accesses this data in memory, compares it with data received from the CGM and acts accordingly.

In one embodiment, such an automatic system for insulin delivery is referred to as an artificial pancreas system that provides closed loop or semi-closed loop therapy to the patient to approach or mimic the natural functions of a healthy pancreas. In such a system, insulin doses are calculated based on the CGM readings and are automatically delivered to the patient based on the CGM reading(s). For example, if the CGM indicates that the user has a high blood glucose level or hyperglycemia, the system can calculate an insulin dose necessary to reduce the user's blood glucose level below a threshold level or to a target level and automatically deliver the dose. Alternatively, the system can automatically suggest a change in therapy such as an increased insulin basal rate or delivery of a bolus, but can require the user to accept the suggested change prior to delivery. If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, suggest that the user, e.g., ingest carbohydrates and/or automatically take other actions and/or make other suggestions as may be appropriate to address the hypoglycemic condition, singly or in any desired combination or sequence. In some embodiments, multiple medicaments can be employed in such a system such as a first medicament, e.g., insulin, that lowers blood glucose levels and a second medicament, e.g., glucagon, that raises blood glucose levels.

However, because CGM devices estimate blood glucose levels from analyzing interstitial plasma or fluid rather than blood as with blood glucose monitors that utilize a sample of blood obtained from, e.g., a finger stick, CGM devices generally are not as well-suited for accurate blood glucose monitoring. To ensure that a CGM device is estimating the user's glucose level as reliably and accurately as possible, such devices require a user to calibrate with an actual blood sample several times a day that is then used to compare the user's actual blood glucose level with the glucose levels measured by the CGM. Such calibration, however, is only done periodically, such as every 12 hours. Embodiments of the present invention therefore incorporate solutions for mitigating the risk of automatically dosing insulin or other medicament to patients based on potentially inaccurate CGM data. Alternatively, the embodiments described herein can be utilized in automatically calculating insulin or other medicament doses based on the CGM data that are suggested to the user and require user interaction for delivery.

Figure 5:
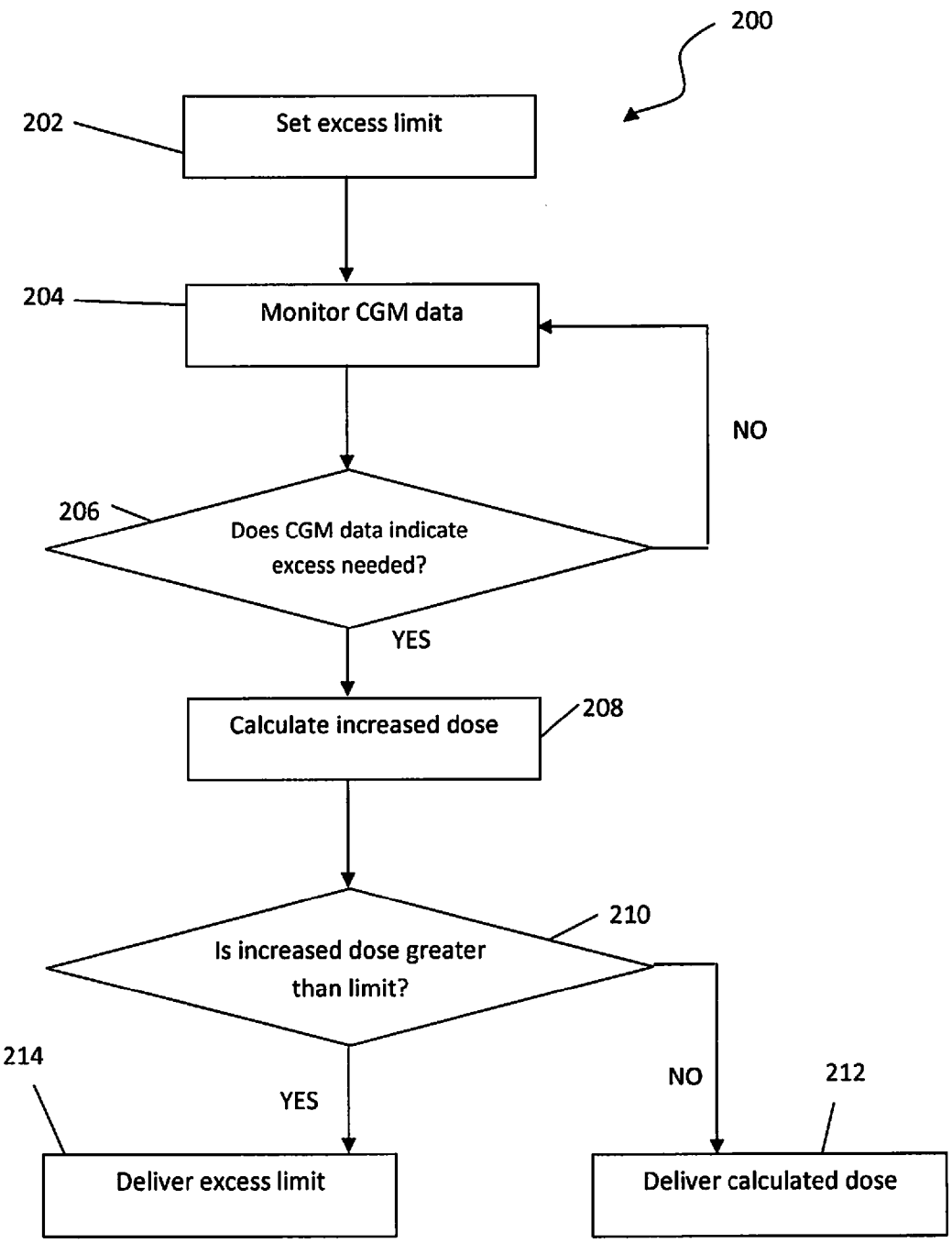
FIG. 5 is a flowchart of a method of mitigating risk in automated medicament dosing according to an embodiment of the present invention.

Referring now to FIG. 5, a method of mitigating risk in automatic insulin or other medicament dosing based on CGM data 200 that can be utilized with infusion pumps such as described herein is shown. This method 200 mitigates the risk of excessive medicament being delivered based on CGM readings indicating a higher glucose level than the user's actual blood glucose level by limiting the amount by which the device can increase a dose of medicament from previous doses.

At step 202, a limit on the excess medicament that can be delivered can be set. In one embodiment, the limit can be based on a percentage or multiple of the current basal rate. For example, a maximum increase in the basal rate could be set to be, for example, one and one half (1.5) or two (2) times the current basal rate. In certain embodiments, the increase in basal rate could be any amount up to five (5) times the current basal rate, such that the percentage based limit on the increase could be anywhere between an additional 0% (i.e., no increase is allowed) and 500% of the basal rate.

In another embodiment, the limit can be a fixed amount of medicament above a previous bolus amount. For example, the maximum increase could be three (3) units of, e.g., insulin so that if a user delivers a ten (10) unit meal bolus, the system can only deliver an additional three units of insulin if CGM data indicate additional insulin is needed over a pre-defined time period, such as, for example, five (5) hours. In certain embodiments, the pre-defined time period can be any time period up to ten (10) hours. In one embodiment, the user can set a custom pre-defined time period either as a global parameter or for specific boluses. The amount of additional insulin that may be delivered can vary based on an insulin sensitivity of a user. In one embodiment, the maximum amount of additional insulin that the system can allow to be programmed as a limit is 25 units of insulin.

In a further embodiment, the maximum increase can be a percentage of the most recently delivered bolus. For example, the limit could be set at 30% of a previous bolus dose, such that if a previous bolus of ten (10) units of, e.g., insulin was delivered, the system could not deliver more than another three (3) units over a subsequent time period. In certain embodiments, the time period can be user-defined and can be any time period up to ten (10) hours. The percentage of a previous bolus that could be delivered can vary, but in certain embodiments a maximum percentage that can be programmed as the limit is 100% of the previous bolus amount.

The limit set at step 202 can be defined after each bolus is delivered or basal rate is set or globally as a parameter for all boluses and/or basal rates. For example, the user could set a limit on subsequent additional medicament at 30% for all boluses. Alternatively or in addition, the user could set the amount limit or percentage limit for an individual bolus. In some embodiments, the user can also set the amount of time after the bolus is delivered or basal rate is set that the limit applies. A limit on the increase in basal rate based on CGM data can also be set globally for all basal rates or each time a different basal rate is begun.

After the excess medicament limit it set, the insulin pump device monitors the data from the CGM following the initial medicament delivery at step 204. The device determines whether the CGM data indicates that excess medicament should be delivered at step 206. If not, the device continues monitoring. If it is determined that excess should be delivered, the device determines the necessary correction bolus or increased basal rate to lower the user's blood glucose based on the data at step 208. The additional medicament is then compared at step 210 to the previously set excess medicament limit. If the excess medicament is less than the limit, the insulin is delivered at step 212. If the excess medicament is greater than the preset limit, the medicament delivered will be reduced to the limit and delivered at step 214. In some embodiments, an intermediate step may notify the user that the device has calculated a correction dose based on the CGM data that is greater than the limit and that only the amount of the limit will be delivered. Such a message may also suggest that the user calibrate the CGM. If the user then calibrates the CGM, in some embodiments an additional amount of the originally calculated correction bolus can be delivered due to the increased CGM accuracy resulting from the calibration.

Figure 6:
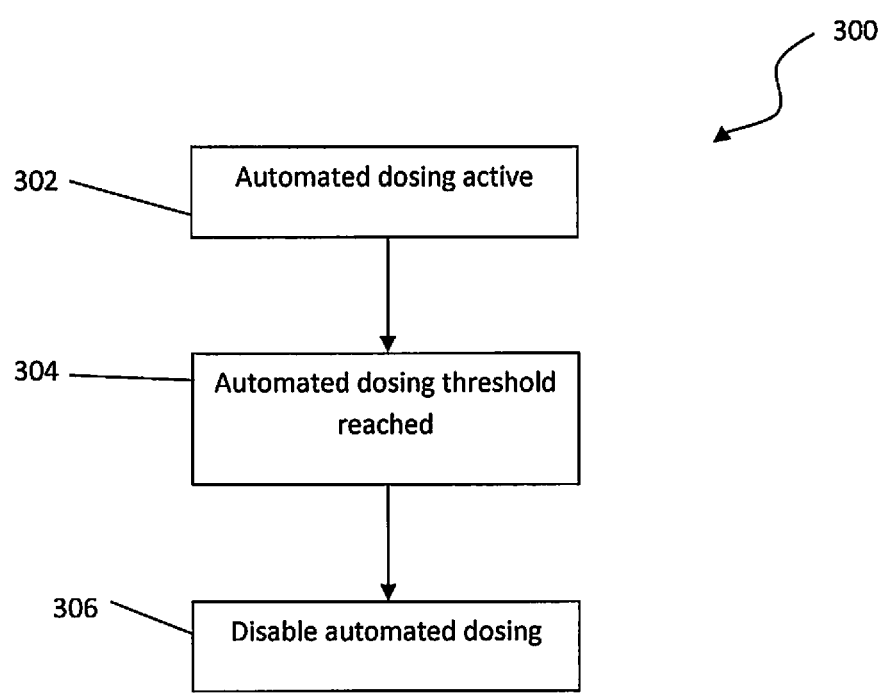
FIG. 6 is a flowchart of a method of mitigating risk in automated medicament dosing according to an embodiment of the present invention.

FIG. 6 depicts an embodiment of a method 300 of mitigating risk in automatic medicament dosing based on CGM data that can be utilized with infusion pumps such as described herein. This method 300 limits the amount of time that automatic dosing of medicament is permitted based on CGM data based on one or more parameters. At step 302, the system is operating in auto-dose mode as described herein in which CGM data is monitored and medicament is automatically calculated and/or dosed as indicated by the data. At step 304, a threshold or limit on when automated dosing is permitted to occur is reached. In response to the threshold being reached, automated dosing is disabled at step 306. In some embodiments, the user or, e.g., caregiver, can be notified on a user interface of the pump device or on a user interface of another device that automated dosing has been disabled as a result of the limit and, in some embodiments, requested to calibrate the CGM.

A number of different parameters can be utilized to set the threshold at which automated dosing will be disabled. In one embodiment, the threshold can be set based on time that has elapsed since the most recent calibration of the CGM upon which the automated dosing is based given that CGM reliability is known to decrease the longer it has been since calibration. Automatic dosing can be automatically disabled when the CGM device requires an additional calibration, which can be a time period based on the specific CGM device, and can automatically begin again once the calibration is performed. Automated dosing can also be automatically disabled based on a set time period after the last calibration until a subsequent calibration is performed, such as, for example, 12 hours, 24 hours, or a time between 12 and 24 hours.

In another embodiment, automated dosing can be disabled when the CGM has a predicted maximum error above a certain threshold value. Such error values typically can be obtained from the CGM manufacturer and are based on the time that has elapsed since the last calibration, the characteristics of the CGM, and can also take into account the accuracy of the system at the last calibration. For example, the system may disable automated dosing if the maximum error exceeds, e.g., 50 mg/dL or 100 mg/dL. Alternatively, automated dosing can be disabled if the predicted maximum error were capable of causing an unsafe drop in blood glucose, such as below 70 mg/dL. For example, if the system is attempting a dose to lower the patient's blood glucose level to 180 mg/dL and the system has a maximum error of 115 mg/dL, the patient's blood glucose could potentially be dropped to 65 mg/dL and auto-dosing would be disabled. In certain embodiments, this safe threshold can have various values, such as 70 mg/dL, 100 mg/dL, or any value in between.

In a further embodiment, automated dosing can be disabled when a maximum threshold value of a blood glucose level deviation between the blood glucose level at the previous calibration and the estimated blood glucose level based on the CGM data is reached. For example, if the CGM data indicate a blood glucose level deviation of more than 100 mg/dL compared to the actual blood glucose level obtained at the most recent calibration, the system can automatically disable the automated dosing. In other embodiments, the blood glucose level deviation at which automated dosing is disabled can be, for example, anywhere between 100 mg/dL and 300 mg/dL In each of the above cases, automated dosing is disabled because the system determines, via these methods, that the CGM data is likely too unreliable to be relied upon for automatic delivery of insulin.

Figure 7:
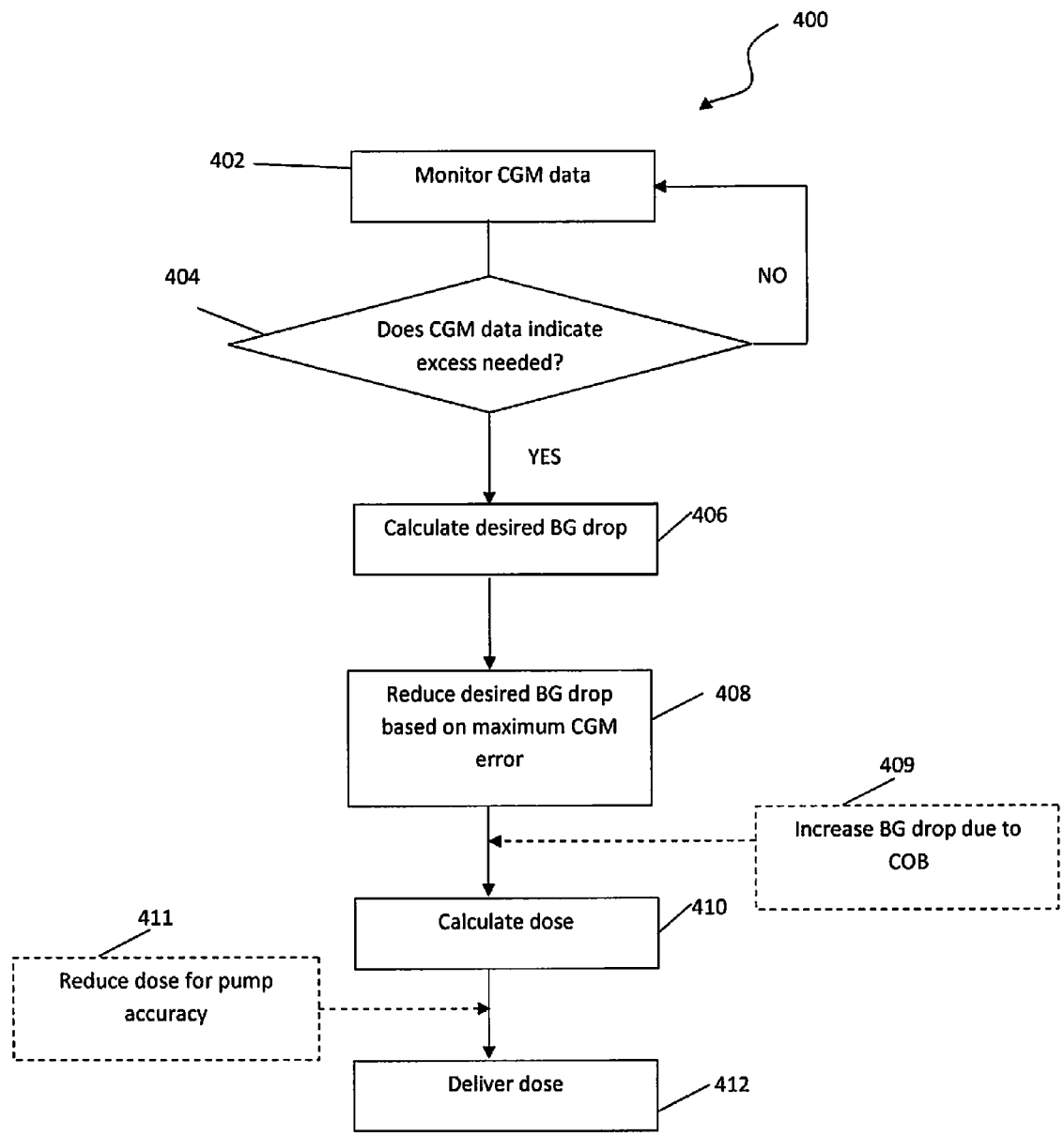
FIG. 7 is a flowchart of a method of mitigating risk in automated medicament dosing according to an embodiment of the present invention.

In a further embodiment, mitigating risks associated with automated dosing based on CGM data can be accomplished via an algorithm that utilizes the current maximum CGM error to determine whether or not it is safe to auto-dose. FIG. 7 depicts a method of mitigating risk of automated dosing 400 according to such an embodiment.

As shown in FIG. 7, the pump monitors the patient's CGM data at step 402 and continues to do so until the CGM data indicates that a dose of, for example, insulin is needed at step 404. Once it is determined that a dose is needed, the desired blood glucose level drop is calculated at step 406. This desired BG level drop is calculated as the current CGM BG level reading minus the target blood glucose level. For example, if the target blood glucose level is 180 mg/dL and the current CGM BG level reading indicates that patient is at 230 mg/dL, the desired BG level drop would be 50 mg/dL.

Next, an attempted BG level drop is calculated based on the desired BG level drop and the maximum CGM error at step 408. As noted above, the maximum CGM error is based on the time since calibration and the characteristics of the CGM and can generally be found in data published by, e.g., the CGM manufacturer. For example, the maximum error at a given time could be 30 mg/dL. The attempted BG level drop can them be calculated as:

Desired BG Level Drop−Maximum CGM Error−
(IOB*ISF)=Attempted BG Level Drop

In the above equation, insulin already present in the patient's system is accounted for in the final variable, which is the product of insulin on board (IOB, the estimated amount of insulin still active in the patient's body that will lower blood sugar in the future) and the patient's insulin sensitivity factor (ISF, the amount of blood glucose drop for a given amount of insulin for the patient). For example, if the patient had no insulin on board, the attempted BG level drop in this example would be the desired BG level drop of 50 mg/dL minus the maximum CGM error of 30 mg/dL, for 20 mg/dL. The system would therefore attempt to drop the patient's blood glucose level by 20 mg/dL to account for the maximum error of the CGM. Therefore, the attempted BG level drop will always be less than or equal to the desired BG level drop. The insulin dose delivered to the patient is then calculated at step 410 by multiplying the attempted BG level drop by the patient's insulin sensitivity factor (typically in units per mg/dL) and the dose is delivered to the patient at step 412. For example, if the patient's ISF is 1 unit per 40 mg/dL, the device would deliver 0.5 units of insulin to the patient to attempt to lower the patient's blood glucose level 20 mg/dL.

In the above-stated example, if the maximum CGM error were not accounted for and CGM were in fact off by the maximum error and instead of being at 230 mg/dL the patient was at 200 mg/dL, the desired BG level drop of 50 mg/dL would drop the patient's blood glucose level to 150 mg/dL rather than 180 mg/dL. So while the system would be inaccurate, the patient's resulting blood glucose level would not be medically concerning. However, if the maximum CGM error were 150 mg/dL and the CGM indicated a patient blood glucose level of 300 mg/dL potentially serious medical issues could arise without accounting for the CGM error. The system would theoretically give the patient enough insulin to lower the blood glucose level 120 mg/dL, i.e., down to 180 mg/dL. If the system error were at its maximum the patient's blood glucose level would actually be only 150 mg/dL and therefore the extra insulin delivered would lower the patient's blood glucose level to a dangerous 30 mg/dL. Thus, by limiting the amount of extra insulin that can be delivered based on the maximum CGM error as described above, such potential medical issues can be avoided while still generally allowing automated dosing of insulin based on CGM data.

In certain embodiments, the above calculations can also incorporate a "safe threshold" that defines a value below which blood glucose would be considered unsafe in addition to the target threshold to which the blood glucose level is attempted to be lowered. For example, the treatment may attempt to lower the blood glucose level to 180 mg/dL while also having a safe threshold of 100 mg/dL. The reduction in the attempted BG level drop based on the maximum CGM error can be reduced based on these values. This is calculated as set forth below.

Desired Level BG Drop−(Maximum CGM Error−(Target−Safe Threshold))=Attempted Level BG Drop IOB would also be taken into account in this calculation as set forth above. Note that the term in parentheses, (Maximum CGM Error−(Target−Safe Threshold)), is only factored into the calculation if it is positive so that it reduces the insulin dose. If the term is negative it is removed from the equation so that it does not increase the insulin dose. This additional factor allows treatment to actually reach the target value because in situations where the CGM error is low and there is no danger of reaching an unsafe blood glucose level, the error is essentially discarded and a full desired dose is delivered rather than always reducing the dose based on the CGM error.

In some embodiments, an additional step that accounts for carbohydrates consumed by the user can be incorporated into the above-described method 400. This step utilizes carbohydrates on board (COB), or the estimated amount of carbohydrates that the patient has eaten that have not yet been metabolized. This variable accounts for a future rise of blood glucose level due to food consumed and will tend to raise the amount of injected insulin (which may not always be desirable given the CGM accuracy issues discussed herein). COB can optionally be factored into the algorithm at step 409 in between calculating the attempted BG level drop at step 408 and calculated the insulin dose at step 410. The attempted BG level drop with carbohydrates is calculated at this step by the equation:

Attempted BG Level Drop+(COB*(CF/ISF)=Attempted BG Level Drop with Carbs, in which CF is the carbohydrate factor for the patient, or the amount of insulin required to metabolize a given amount of carbohydrates, and ISF is the insulin sensitivity factor described above. Utilization of COB in the insulin dosing algorithm will tend to bring the patient's blood glucose level within acceptable parameters more quickly by accounting for consumed carbohydrates in advance. However, the patient's blood glucose level would eventually come back into line regardless, because any subsequent rise in blood glucose level from the carbohydrates being metabolized would later be accounted for with an additional insulin dose. Therefore this step is not strictly necessary in order to safely auto-dose insulin based on CGM data.

Another optional step in the method 400 depicted in FIG. 7 includes adjusting the insulin dose based on the accuracy of the insulin pump that delivers the dose. Insulin pumps are labeled as to their delivery accuracy, typically in terms of a percent delivery accuracy either in general or varying based on particular delivery rates and volumes. In such an embodiment, at step 411 after the initial insulin dose calculation at step 410, the insulin dose is reduced based on the pump accuracy to provide additional assurance that the delivered dose does not produce hypoglycemia.

FIGS. 5-7 represent various embodiments of methods of mitigating risk in automatic dosing of medicaments such as insulin based on CGM data. It should be noted that these methods are not mutually exclusive and that any of the methods could be employed, in whole or in part, simultaneously with any of the other methods. It should further be noted that although primarily described with respect to medicaments such as insulin that lower blood glucose level, these methods could be adapted for use with additional or other medicaments that have other effects on the body, such as medicaments, e.g., glucagon, that raise blood glucose level, which will cause a corresponding change in various aspects of the methods, e.g., replacing BG drop with BG increase.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 8,287,495; 8,408,421 and 8,448,824; commonly owned U.S. Patent Publication Nos. 2009/0287180; 2010/0008795; 2010/0071446; 2010/0218586; 2012/0123230; 2013/0053816; 2013/0159456; 2013/0306191; 2013/0324928; 2013/0332874; 2013/0283196; 2013/0331790; 2013/0331778; and commonly owned U.S. patent application Ser. Nos. 13/800,387; 13/800,453; 13/800,595; 13/827,383; 13/829,115; 13/832,531; 13/832,841; 13/837,661; 13/837,777; 13/838,084; 13/841,432; 13/842,005; 13/842,990 and 13/923,556; and commonly owned U.S. Provisional Application Ser. Nos. 61/875,979, 61/911,576, 61/920,902, 61/920,914, 61/920,923, 61/920,932; 61/920,940; 61/990,501; and 62/030,933.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872, 200; 6,813,519; 6,641,533; 6,554,798; 6,551,276; 6,295,506; and 5,665,065. Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A portable infusion pump, comprising:
a delivery mechanism adapted to facilitate a delivery of a medicament to a user;
a memory adapted to store one or more parameters relating to the delivery of the medicament;
a communications device adapted to receive information from a continuous glucose monitor; and
a processor functionally linked to the delivery mechanism and the memory and to the communications device to obtain the information from the continuous glucose monitor, the processor configured to:
monitor the information received from the continuous glucose monitor;
determine from the information received from the continuous glucose monitor that an additional amount of the medicament should automatically be delivered to the user;
review at least one parameter of the one or more parameters stored in the memory that relates to mitigating risk in automatically delivering the medicament based on the information received from the continuous glucose monitor;
determine whether the additional amount of the medicament can be delivered to the user in view of the at least one parameter that relates to mitigating risk; and
cause the delivery mechanism to deliver the additional amount of the medicament if it is determined that the additional amount of the medicament can be delivered to the user,
wherein the at least one parameter that relates to mitigating risk in automatically delivering the medicament includes an excess medicament amount limit defining a maximum amount by which the medicament delivered to the user can be increased, and determining whether the additional amount of the medicament can be delivered includes comparing the additional amount of the medicament to the excess medicament amount limit.

2. The portable infusion pump of claim 1, wherein it is determined that all of the additional amount of the medicament can be delivered to the user if the additional amount of the medicament is below the excess medicament amount limit.

3. The portable infusion pump of claim 1, wherein the processor is further configured, if it is determined that the additional amount of the medicament is greater than the excess medicament amount limit, to control the delivery mechanism to deliver a portion of the additional amount of the medicament equal to the excess medicament amount limit.

4. The portable infusion pump of claim 1, wherein the excess medicament amount limit is determined as a percentage of a current basal rate currently in use to deliver the medicament to the user.

5. The portable infusion pump of claim 4, wherein the percentage is user-selectable and between 0% and 500% of the current basal rate.

6. The portable infusion pump of claim 1, wherein the excess medicament amount limit is determined as a fixed amount of the medicament above a previously delivered bolus amount of the medicament or a percentage of the previously delivered bolus amount of the medicament.

7. The portable infusion pump of claim 6, wherein the excess medicament amount limit is utilized for a predefined time period after delivery of the previous bolus amount, and one or more of the fixed amount, percentage and predefined time period are user-selectable.

8. The portable infusion pump of claim 1, wherein the additional amount of the medicament is determined as an amount of the medicament necessary to lower the user's blood glucose level to a target blood glucose level or below a high blood glucose threshold.

9. The portable infusion pump of claim 1, further comprising presenting a recommendation to the user on a user interface of the portable infusion pump to calibrate the continuous glucose monitor if it is determined that any portion of the additional amount of the medicament cannot be delivered to the user.

10. A portable infusion pump, comprising:
a delivery mechanism adapted to facilitate a delivery of a medicament to a user;
a memory adapted to store one or more parameters relating to the delivery of the medicament;
a communications device adapted to receive information from a continuous glucose monitor; and
a processor functionally linked to the delivery mechanism and the memory and to the communications device to obtain the information from the continuous glucose monitor, the processor configured to:
monitor the information received from the continuous glucose monitor;
determine from the information received from the continuous glucose monitor that an additional amount of the medicament should automatically be delivered to the user;
review at least one parameter of the one or more parameters stored in the memory that relates to mitigating risk in automatically delivering the medicament based on the information received from the continuous glucose monitor;
determine whether the additional amount of the medicament can be delivered to the user in view of the at least one parameter that relates to mitigating risk; and
cause the delivery mechanism to deliver the additional amount of the medicament if it is determined that the additional amount of the medicament can be delivered to the user,
wherein the at least one parameter that relates to mitigating risk in automatically delivering the medicament includes a threshold relating to predicted accuracy of the continuous glucose monitor after which automatic adjustment of the delivery of the medicament based on the information from the continuous glucose monitor is not permitted.

11. The portable infusion pump of claim 10, wherein the threshold is set as an amount of time that has elapsed since a most recent calibration of the continuous glucose monitor.

12. The portable infusion pump of claim 10, wherein the threshold is set as a maximum predicted error of the continuous glucose monitor.

13. The portable infusion pump of claim 10, wherein the threshold is set as a maximum difference between a blood glucose level at a most recent calibration of the continuous glucose monitor and a current estimated blood glucose level of the continuous glucose monitor.

14. A portable infusion pump, comprising:
- a delivery mechanism adapted to facilitate a delivery of a medicament to a user;
- a memory adapted to store one or more parameters relating to the delivery of the medicament;
- a communications device adapted to receive information from a continuous glucose monitor; and
- a processor functionally linked to the delivery mechanism and the memory and to the communications device to obtain the information from the continuous glucose monitor, the processor configured to:
  - monitor the information received from the continuous glucose monitor;
  - determine from the information received from the continuous glucose monitor that an additional amount of the medicament should automatically be delivered to the user;
  - review at least one parameter of the one or more parameters stored in the memory that relates to mitigating risk in automatically delivering the medicament based on the information received from the continuous glucose monitor;
  - determine whether the additional amount of the medicament can be delivered to the user in view of the at least one parameter that relates to mitigating risk; and
  - cause the delivery mechanism to deliver the additional amount of the medicament if it is determined that the additional amount of the medicament can be delivered to the user,
- wherein the at least one parameter that relates to mitigating risk in automatically delivering the medicament includes a parameter utilizing an algorithm executed by the processor that determines whether or not the additional amount of the medicament can be delivered utilizing an estimated current maximum error of the continuous glucose monitor.

* * * * *